Figure 1:
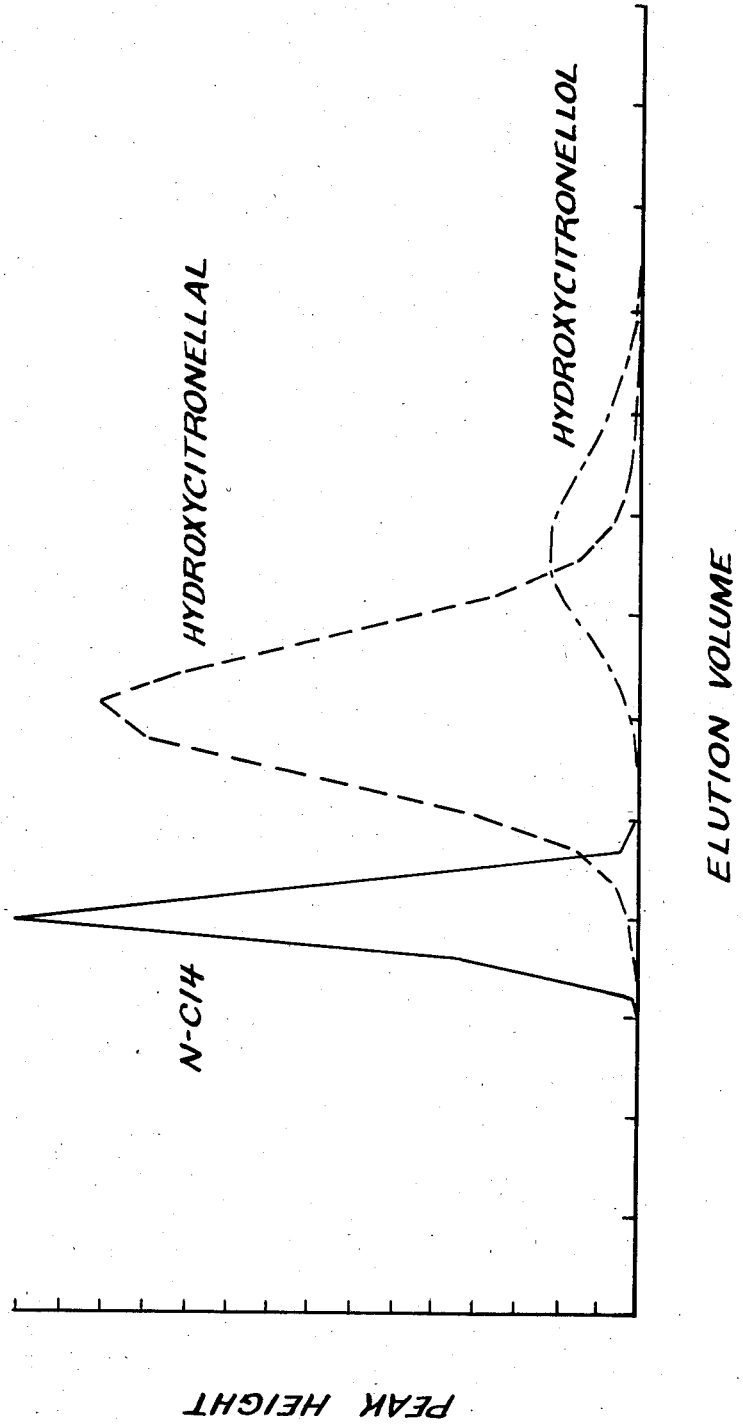

United States Patent [19]

Zinnen

[11] Patent Number: 4,605,783

[45] Date of Patent: Aug. 12, 1986

[54] PROCESS FOR SEPARATING MONOTERPENES

[75] Inventor: Hermann A. Zinnen, Evanston, Ill.

[73] Assignee: UOP Inc., Des Plaines, Ill.

[21] Appl. No.: 714,404

[22] Filed: Mar. 21, 1985

[51] Int. Cl.[4] .................. C07C 45/78; C07C 45/79
[52] U.S. Cl. .................. 568/492; 568/810; 568/868; 568/872
[58] Field of Search ............ 568/492, 854, 868, 869, 568/872, 810

[56] References Cited

U.S. PATENT DOCUMENTS

| | | | |
|---|---|---|---|
| B 426,274 | 1/1976 | Hedge | 568/810 |
| 2,564,717 | 8/1951 | Olsen | 568/872 |
| 2,916,525 | 12/1959 | Giesen et al. | 568/872 |
| 2,985,589 | 5/1961 | Broughton | 568/810 |
| 3,201,491 | 8/1965 | Stine et al. | 260/676 |
| 3,265,750 | 8/1966 | Peck | 260/676 |
| 3,510,423 | 5/1970 | Neuzil et al. | 208/310 |
| 3,663,638 | 5/1972 | Neuzil | 260/674 |
| 3,665,046 | 5/1972 | Rosset | 260/674 |
| 3,668,266 | 6/1972 | Chen | 260/674 |
| 3,700,744 | 10/1972 | Berger et al. | 260/668 |
| 3,734,974 | 5/1973 | Neuzil | 260/674 |
| 3,894,109 | 7/1975 | Rosback | 260/674 |
| 4,054,555 | 10/1977 | Ackermann et al. | 568/492 |
| 4,450,294 | 5/1984 | Feldman | 568/492 |
| 4,456,774 | 6/1984 | Sherman et al. | 568/872 |

FOREIGN PATENT DOCUMENTS

| | | | |
|---|---|---|---|
| 2538381 | 6/1984 | France | 568/872 |
| 0001296 | 1/1981 | Japan | 568/492 |
| 0113725 | 9/1981 | Japan | 568/492 |

Primary Examiner—Werren B. Lone
Attorney, Agent, or Firm—Thomas K. McBride; John F. Spears, Jr.; John G. Tolomei

[57] ABSTRACT

An adsorptive method of separating alcohols and aldehydes or ketones and alcohols of monoterpenes is disclosed. The method uses an X-type zeolite containing sodium and potassium cations to selectively adsorb the alcohols thereby allowing recovery of an aldehyde or ketone raffinate stream and, after desorption, an alcohol extract stream. The method is suitable for feed mixtures containing individual or multiple monoterpenoid components.

12 Claims, 3 Drawing Figures

PROCESS FOR SEPARATING MONOTERPENES

BACKGROUND OF THE INVENTION

1. Field of the Invention

The field of art to which this invention pertains is the solid bed adsorptive separation of terpenoids. More specifically, the invention relates to a process for separating monoterpene alcohols from a feed mixture comprising monoterpene alcohols, and monoterpene aldehydes and/or ketones by adsorptive separation using crystalline aluminosilicate adsorbents.

2. Background Information

The use of crystalline aluminosilicates to perform hydrocarbon separation is well known in the separation art. Examples of such separations are disclosed in U.S. Pat. Nos. 2,985,589 and 3,201,491 wherein a type A zeolite is used to separate normal paraffins from branched chain paraffins. The use of faujasites to separate olefinic hydrocarbons from paraffinic hydrocarbons is described in U.S. Pat. Nos. 3,265,750 and 3,510,423. These adsorbents allow a separation based on the physical size differences in the molecules by allowing the smaller or normal hydrocarbons to be passed into the cavities within the zeolitic adsorbent, while excluding the larger or branched chain molecules.

In addition to being used in processes for separating hydrocarbon types, adsorbents comprising type X or Y zeolites have also been employed in processes to separate individual hydrocarbon isomers. In the processes described, for example, in U.S. Pat. Nos. 3,626,020 to Neuzil, 3,663,638 to Neuzil, 3,665,046 to deRosset, 3,668,266 to Chen et al., 3,686,343 to Bearden Jr. et al., 3,700,744 to Berger et al., 3,734,974 to Neuzil, 3,894,109 to Rosback, 3,997,620 to Neuzil and B 426,274 Hedge, particular zeolitic adsorbents are used to separate the para isomer of bialkyl substituted monocyclic aromatics from the other isomers, particularly paraxylene from other xylene isomers.

Turning specifically to the class of compounds of this invention, terpenoids include the saturated or partially saturated isomers of terpenes as well as derivatives such as alcohols, ketones, aldehydes, esters, etc. Terpenes are chiefly derived from essential oils. The oxygenated terpenoid derivatives are particularly important flavor and perfume materials. Most commonly used terpenes are separated by fractional distillation. However, terpene compounds are heat sensitive, thus fractionation often requires energy intensive vacuum distillation techniques to avoid degradation of components.

Apart from fractionation, adsorptive separation techniques have been used to isolate individual terpenes from essential oils and other terpene containing feedstocks. U.S. Pat. No. 2,760,993 teaches the use of activated clay, magnesia, charcoal and alumina in conjunction with polar solvents to separate menthol from mint oils. Preparation of a terpeneless essential oil by removal of terpenes through distillation and adsorption onto neutral alumina is taught in U.S. Pat. No. 3,867,262.

Applicant has found that monoterpenoids can be separated by adsorptive separation techniques using an X-type zeolite.

SUMMARY OF THE INVENTION

In brief summary the invention is in one embodiment a process for separating an alcohol of a monoterpene from a feed mixture containing alcohols, aldehydes and/or ketones of a monoterpene. The process comprises contacting, in liquid phase at adsorption conditions, the feed with an X-type zeolite adsorbent having sodium or potassium cations at cation exchange sites to selectively adsorb the alcohol component of the feed mixture to the substantial exclusion of the aldehyde and ketone components. The unadsorbed portion of the feed or raffinate component is removed from the adsorbent which is then contacted with a desorbent material at desorption conditions, thereby recovering the monoterpene alcohol or extract component from the adsorbent. In another embodiment the alcohol containing adsorbent is contacted with a hydrocarbon or oxygenated hydrocarbon desorbent material.

Other embodiments of the present invention encompass specific feed mixtures, desorbents, flow schemes and operating conditions, all of which are hereinafter disclosed in the following discussion of each of the facets of the present invention.

DESCRIPTION OF THE INVENTION

Suitable feed mixtures are mixtures of one or more monoterpenoid alcohols and its corresponding aldehyde or ketone. The term terpenoids refers generally to the class of saturated, partially saturated or derivitized terpenes. In turn, terpenes found in most living plants are usually considered derivatives of isopene. In most terpene compounds, the isoprene units are arranged in head to tail fashion. Classification of terpenes is done on the basis of isoprene unit and degree or lack of ring structure. Monoterpenes contain two isoprene units arranged in either an open chain or ring structure.

The corresponding terpenoids of more well known monoterpenes include citronellal, citranellol, geranial, geraniol, hydroxycitronellal, and hydroxycitronellol. These chemicals have desirable fragrance properties and are most commonly used in perfumery. While many of these chemicals are available in natural form, they may also be derived synthetically. Derivation of perfume chemicals usually begins with beta-pinene found in crude sulfate turpentine. Thermal rearrangement of beta-pinene yields myracene which is an important intermediate for many fragrance compounds. Hydrochlorination of myracene under appropriate conditions followed by heating with sodium acetate will yield geraniol and nerol acetates after which saponification and distillation will yield geranoil and nerol. Geraniol and nerol may be rearranged over a copper catalyst to provide citronellol and, with further hydration, hydroxycitronellol.

Aldehyde or ketone and alcohol mixtures of a monoterpene are often obtained in the course of producing one component from another. For instance, citronellal, which can be artificially derived or obtained from the rectification of citronella oil, is often reduced to produce citronellol thereby yielding a mixture of the two. Another example is the synthesis of citral by the oxidative dehydrogenation of the geometric isomers geranoil and nerol to yield cis- and trans-citrals (neral and geranial) in mixture with geraniol and nerol.

The aforementioned examples of monoterpenoid mixtures containing aldehydes and alcohols is by no means exhaustive, but only serves to show possible sources of feed mixtures to which this invention may be applied.

This invention provides an adsorptive separation method for separating such alcohol/aldehyde and alcohol/ketone mixtures of monoterpenes regardless of source. Thus suitable feed mixtures will contain one or more cyclic or acyclic monoterpenoid alcohols and its corresponding aldehyde and/or ketone. Hence a monoterpenoid may contain a single alcohol and aldehyde combination such as hydroxycitronellol and hydroxycitronellal or mixtures of corresponding monoterpenoids, for example, nerol-neral and geraniol-geranial.

The operability of the process disclosed herein incorporates the discovery that alcohol monoterpenoids are preferentially adsorbed from alcohol and monoterpenoid aldehyde and/or alcohol feed mixtures by contact with an X faujasite having suitable cations. It was further discovered that sodium or potassium cations provide the X zeolite with the necessary adsorptive properties.

While the selectivity properties of an adsorbent are essential to the success of an adsorptive separation process, additional properties are recognized as highly desirable, if not absolutely necessary, to the successful operation of a selective adsorption process. In summary, these characteristics are: adsorptive capacity for some volume of an extract component per volume of adsorbent; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract component largely determines the efficiency of a process; the higher the adsorbent's capacity for an extract component the better is the adsorbent. Increased capacity of a particular adsorbent makes it possible to reduce the amount of adsorbent needed to separate the extract component contained in a particular quantity of feed mixture. A reduction in the amount of adsorbent required for a specific adsorptive separation reduces the cost of the separation process.

The second necessary adsorbent characteristic is the ability of the adsorbent to separate components of the feed; or, in other words, that the adsorbent possesses adsorptive selectivity, (B) for one component as compared to another component. Selectivity (B) is expressed not only for one feed component as compared to another but also between a feed mixture component and a desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivites permit a smaller amount of adsorbent to be used in the process. Ideally desorbent materials should have a selectivity equal to about 1 or less than 1 with respect to all extract component so that all of the extract components can be extracted as a class and all raffinate components clearly rejected into the raffinate stream.

The third important characteristic is the rate of exchange or the relative rate of desorption of the extract component. Faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

The type X faujasites which comprise the adsorbents of this invention are known more generally as zeolites or crystalline aluminosilicates. Crystalline aluminosilicates or molecular sieves, as often referred to by those skilled in the art, exhibit various mechanisms for separating different molecules. The most basic action of these materials is a sieving function in the separation of larger molecules from smaller molecules. In the separation of aromatic hydrocarbons, isomer separation is generally attributed to differences in electrochemical forces. With the larger and more complicated sugar molecules, the separation mechanism is theorized to consist of combined size exclusion properties and electrostatic forces which as a result of steric properties only exclude certain saccharide molecules from entering the sieve pores. Although no specific theory is adopted as the basis of this invention, the preferential adsorption of the monoterpenoid alcohols in this invention is attributed to differences in hydrophilicity and polarity caused by additional or different functional groups within the monoterpenoids.

The general structure and composition of the X type zeolite used in this invention is disclosed in U.S. Pat. Nos. 2,883,244 and 3,120,007 which describe and define these materials and are herein incorporated by reference. Zeolites as initially prepared or found naturally are made up of alumina and silicon oxides in a hydrated or partially hydrated form which includes cations at cation exchange sites which serve to balance the electronegativity of the molecule. As initially prepared, an X zeolite will contain predominantly sodium cations. It has been found that an X zeolite containing sodium cations is an effective adsorbent for this invention. However, it is possible to replace these sodium cations with potassium cations by well-known ion exchange methods and still obtain a highly effective adsorbent for use in this invention. Exchange of sodium cations may be essentially complete or partial which will yield a mixture of sodium and potassium cations. Typical ion exchange methods involve contacting the zeolite with an aqueous solution of the soluble salt of the cation to be placed on the sieve and, after the desired degree of exchange has taken place, removing the sieve from the solution. The above procedure or other ion exchange procedures may be used to replace sodium cations or remove unwanted cations from the zeolite adsorbent.

The adsorbent may be in the form of particles such as extrudates, aggregates, tablets, macrospheres or granules having a desired particle range, preferably from about 16 to about 60 mesh (Standard U.S. Mesh). Less water content in the adsorbent is advantageous from the standpoint of less water contamination of the product.

In addition to adsorbents, the complete functioning of an adsorption separation process requires a desorbent to remove selectively retained components from the adsorbent. A desorbent material has been defined as any substance capable of removing a selectively adsorbed feed component from an adsorbent. For this invention, suitable desorbents include alcohols, hydrocarbons and ketones. Out of this general class of desorbents those having oxygen functional groups are preferred. Particularly effective desorbents which are most suitable for continuous adsorption processes consist of diethyl ketone, methyl ethyl ketone, 4-methyl-2-pentanone and 1-butanol dissolved in ketone. Although general classes and specific compounds have been mentioned, those skilled in the art are aware of many criteria that govern the choice of a specific desorbent material. Such factors include a selectivity intermediate between that of the extract and raffinate components, compatability with the feed mixture, and separability from the feed mixture. Separability usually requires selection of desorbent material having a boiling point substantially different from the feed components to permit subsequent removal by simple fractionation. A substantially different boiling point for the purpose of most adsorption processes means at least 5° C. difference between the feed mixture components and the desorbent materials. A more thorough discussion of desorbent criteria is contained in U.S. Pat. No. 4,423,279 which is herein incorporated by reference.

The adsorption-desorption operations may be carried out in a dense fixed bed which is alternatively contacted with a feed mixture and a desorbent material in which case the process will be only semicontinuous. In another embodiment, generally referred to as a swing bed system, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

While this invention may be practiced in any type of flow system, the manner of operation will affect desorbent selection. Swing bed systems are less sensitive to desorbent selection so that the process is likely to perform well with any material from the aforementioned broad class of desorbents. However, in adsorptive separation processes which are generally operated continuously at substantially constant pressures and temperatures to ensure liquid phase, the desorbent material relied upon must be selected more judiciously. It is in the continuous separation processes where the previously described class of preferred desorbents will offer the greatest advantages.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate product will be less than about 5 vol. % and more preferably less than about 1 vol. %. The separation means will typically be a fractionation column, the design and operation of which is well known to the separation art.

Although both liquid and vapor phase operations can be used in many adsorptive separation processes, liquid-phase operation is necessary for this process because of the lower temperature and the heat sensitivity of the feed mixture components. In addition, liquid phase operation lowers energy requirements and provides higher yields of extract product. Adsorption conditions will include a temperature range of from about 20° C. to about 250° C., with about 50° C. to about 200° C. being more preferred, and a pressure sufficient to maintain liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a non-adsorbed paraffinic tracer and the particular monoterpenoid feed mixture, all diluted in desorbent, is injected for a duration of several minutes. Desorbent flow is resumed, and the tracer and the feed isomers are eluted as in a liquid-solid chromatographic operation. The effluent can be analyzed by on-stream chromatographic equpiment and traces of the envelopes of corresponding component peaks developed. Alternately, effluent samples can be collected periodically and later analyzed separately by gas chromatography.

From information derived from the chromatographic traces, adsorbent performance can be rated in terms of capacity index for an extract component, selectivity for one hydrocarbon with respect to another, and the rate of desorption of an extract component by the desorbent. The capacity index may be characterized by the distance between the center of the peak envelope of the selectively adsorbed component and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The following examples are presented for illustration purposes and more specifically are presented to illustrate the selectivity of the adsorbents that make the process of the invention possible. Reference to specific desorbent materials, feed mixtures and operating conditions is not intended to unduly restrict or limit the claims of this invention.

EXAMPLE I

In this experiment a pulse test was performed to evaluate the ability of the present invention to separate a monoterpene alcohol from its corresponding aldehyde.

The testing apparatus was the above described pulse test apparatus. For the pulse test, the column was filled with 70 cc of an X zeolite containing sodium cations at cation exchange sites and maintained at a temperature of 130° C. and a pressure sufficient to maintain liquid-phase operations. Gas chromatographic analysis equipment was used to analyze periodically obtained effluent samples in order to determine the composition of the effluent material at given time intervals. The feed mixture employed for this test consists of 1.0 grams of a crude commercial terpene mixture containing approximately 15% hydroxycitronellal and 85% hydroxycitronellol, 0.2 grams of tetradecane, and 1.3 grams of a desorbent material made up of 30 vol. % 1-butanol and the remainder hexane. The operations taking place in the test were as follows. The desorbent material was run continuously at a nominal liquid hourly space velocity (LHSV) of 0.86 which amounted to a 1.00 cc per minute flow rate for the desorbent. At some convenient time interval the desorbent was stopped and the feed mixture was run for a 2.6 minute interval at a rate of 1.0 cc per minute. The desorbent stream was then resumed at 0.86 LHSV and continued to pass into the adsorbent column until all of the feed components had been eluted from the column as determined by observing the chromatograph generated by the effluent material leaving the adsorption column. The sequence of operations usually takes about an hour. The 2.6 minute pulse of feed and subsequent desorption may be repeated in sequence as often as is desired.

The chromatograph tracing obtained is shown in FIG. 1.

As demonstrated by its later appearance the alcohol component was preferentially absorbed. A clear separation between the hydroxycitronellol and hydroxycitronellal component is shown by the pulse test data. Tailing of the hydroxycitronellal curve into the later released hydroxycitronellol is a result of the large concentration of the former component relative to the latter. From these test results a selectivity of 1.64 was calculated which quantitatively demonstrates the achievement of a satisfactory component separation.

EXAMPLE II

Figure 2:
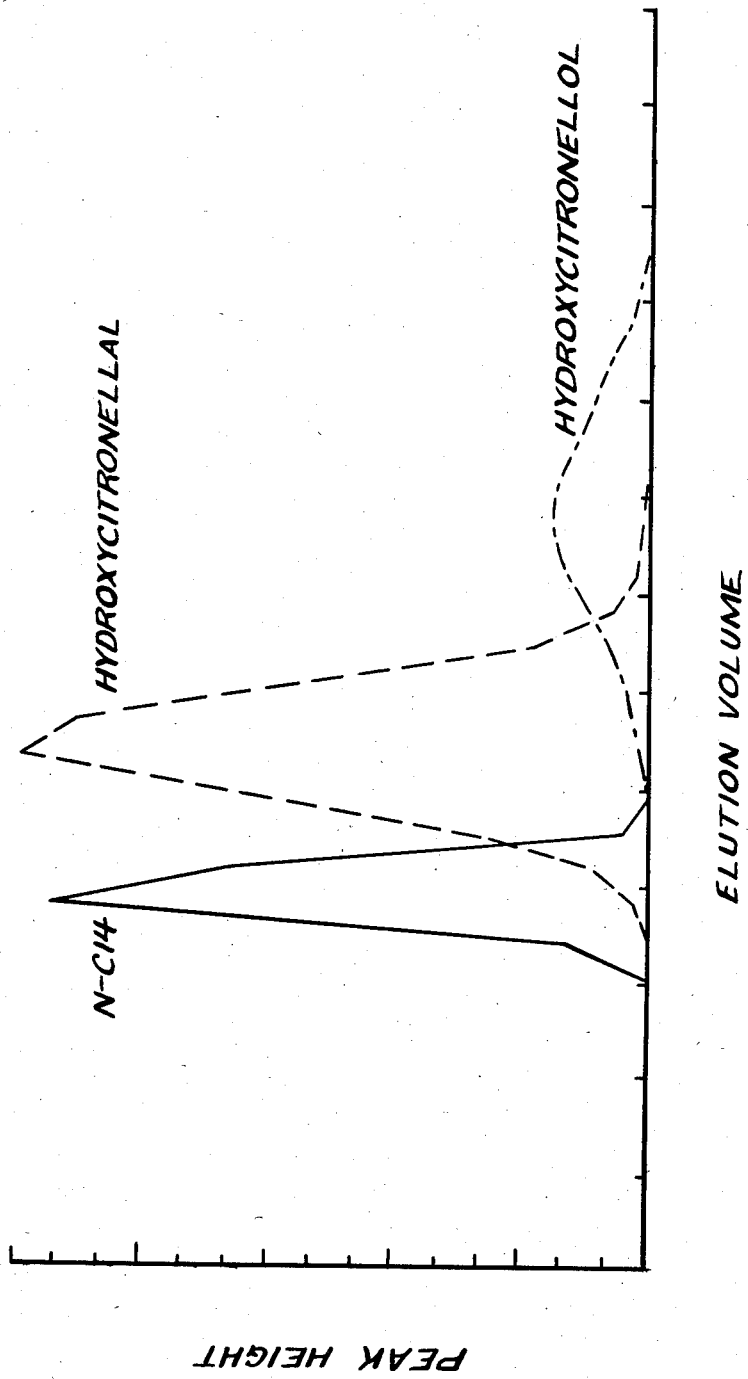

Another pulse test was run in substantially the same manner as Example I except for the use of 70 cc of a potassium exchanged X-type zeolite in the column. The results of this test are shown in FIG. 2. As evident from FIG. 2, the separation of the feed components is more distinct than those obtained in Example I, which is further supported by the calculation of a 2.5 selectivity for Example II. In addition, the half width dimension for the hydroxycitronellal peak was reduced thereby indicating faster rates of adsorption and desorption.

EXAMPLE III

Figure 3:
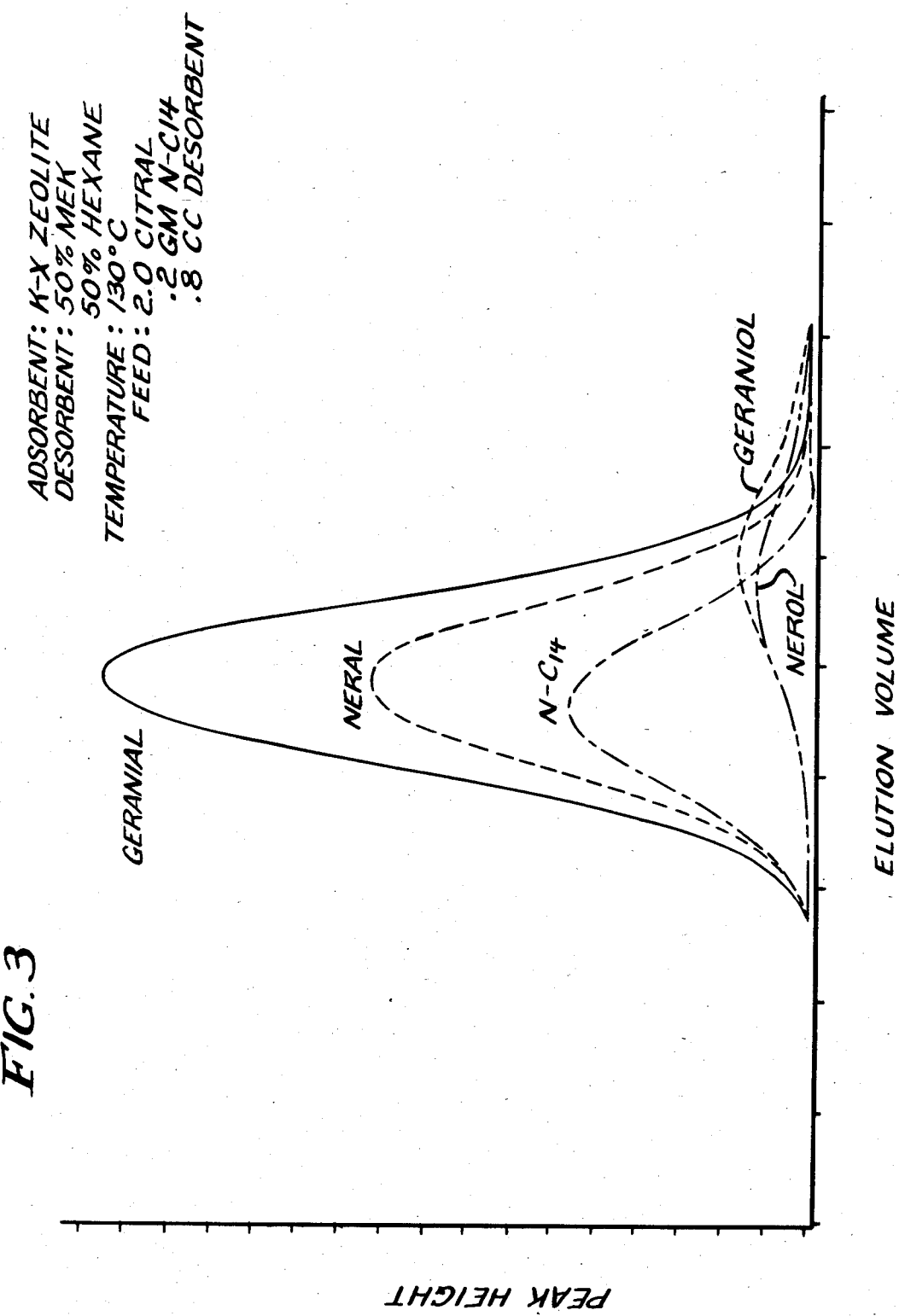

Further testing with a potassium exchanged X zeolite was performed using a commercial feed mixture containing aldehydes and alcohols of two monoterpene hydrocarbons. In this example, a feed mixture made up of 2.0 grams crude terpene mixture, 0.2 grams tetradecane and 0.8 grams of a 50% methyl ethyl ketone-50% hexane desorbent. The terpene component contains approximately 58 vol. % geranial, 5 vol. % geraniol, 31 vol. % neral, and 6 vol. % nerol. Following a procedure paralleling that of Example I, desorbent material was run at a LHSV of 1.05, then the injection of 2.6 cc of feed at a rate of 1.23 cc/minute was accomplished, after which desorbent flow through the column was continued. Graphical results of this test appear in FIG. 3. Again the curves show the later appearance of a mixed alcohol stream peak. Displacement between the centers of the aldehyde and alcohol curves is good, thereby confirming the ability to separate a feed of mixed monoterpenoid alcohols and aldehydes. The separation capability is further confirmed by the calculation of relative selectivities for the various feed components as shown in Table 1.

TABLE 1

| Component Pairs | Selectivity |
|---|---|
| neral/geranial | 1.0 |
| neral/nerol | 7.4 |
| neral/geraniol | 8.1 |
| geranial/nerol | 7.4 |
| geraniol/geranial | 8.1 |
| nerol/geraniol | 1.1 |

EXAMPLES IV-VII

In order to further evaluate the performance of various adsorbents and desorbents in this process, a series of tests were performed using a monoterpenoid mixture of geraniol, nerol, geranial, and neral containing about 11% total alcohols. Conditions and results for the tests are presented in Table 2.

TABLE 2

| Test | Adsorbent | Desorbent | Feed Mixture | Temp. | Flow Rate | Selectivity |
|---|---|---|---|---|---|---|
| 1 | K-X type zeolite | 50 vol. % methyl ethyl ketone 50 vol. % hexane | 1.5 gm monoterpenoid mixture .1 gm tetradecane 1 gm desorbent | 100° C. | 1.20 cc/min. | 7 |
| 2 | K-X type zeolite | 100 vol. % diethyl ketone | 1.5 gm monoterpenoid mixture .1 gm tetradecane .9 gm desorbent | 100° C. | 1.20 cc/min. | 4.1 |
| 3 | Na-X type zeolite | 30 vol. % methyl ethyl ketone 70 vol. % hexane | 2 gm monoterpenoid mixture .2 gm tetradecane .75 gm desorbent | 120° C. | 1.08 cc/min. | 2.75 |
| 4 | Na-X type zeolite | 100 vol. % 4-methyl-2-pentanone | 1.5 gm monoterpenoid mixture .1 gm tetradecane 1 gm desorbent | 100° C. | 1.08 cc/min. | 7 |

The selectivity data of Table 2 establishes that a good separation was achieved for all adsorbent-desorbent combinations tested.

I claim as my invention:

1. A process for separating monoterpene alcohols and aldehydes or ketones of monoterpenes from a feed mixture comprising an aldehyde and/or ketone of a monoterpene and an alcohol of a monoterpene, said process comprising: contacting said mixture at adsorption conditions which include a temperature of from about 25° C. to about 200° C. and a pressure sufficient to maintain liquid phase with an X-type zeolite containing sodium or potassium ions at cation exchange sites thereby selectively adsorbing said monoterpene alcohol to the substantial exclusion of said monoterpene ketone and aldehyde; recovering a nonadsorbed raffinate component substantially free of said monoterpene alcohol; desorbing said selectively adsorbed component with a desorbed material comprising alcohols, ketones, paraffinic hydrocarbons or combinations thereof at desorption conditions in the same range as said adsorption conditions and recovering an adsorbed component substantially free of said monoterpene aldehyde or ketone.

2. The process of claim 1 wherein the desorbent comprises 4-methyl-2-pentanone or diethyl ketone.

3. The process of claim 1 wherein the desorbent material comprises 1-butanol and hexane.

4. The process of claim 1 wherein the desorbent comprises methyl ethyl ketone and hexane.

5. The process of claim 1 wherein the feed mixture comprises hydroxycitronellal and hydroxycitronellol.

6. The process of claim 5 wherein the adsorbent is an X-type zeolite containing potassium ions at cation exchange sites and the desorbent material consists of 1-butanol and hexane.

7. The process of claim 1 wherein the feed mixture comprises geraniol, geranial, nerol and neral.

8. The process of claim 7 wherein said feed mixture is contacted with an X-type zeolite containing potassium ions at cation exchange sites and said selectively adsorbed component is desorbed using a desorbent material comprising methyl ethyl ketone and hexane or diethyl ketone.

9. The process of claim 7 wherein said feed mixture is contacted with an X-type zeolite containing sodium ions at cation exchange sites and said selectively adsorbed component is desorbed using a desorbent comprising 4-methyl-2-pentanone or methyl ethyl ketone and hexane.

10. The process of claim 1 wherein said separation is effected by means of a simulated moving bed flow scheme.

11. The process of claim 10 wherein said simulated moving bed scheme uses countercurrent fluid flow.

12. The process of claim 10 wherein said simulated moving bed scheme uses cocurrent fluid flow.

* * * * *